United States Patent [19]

Goldenberg

[11] 4,036,981

[45] July 19, 1977

[54] METHOD FOR TREATING INFLAMMATION

[75] Inventor: Marvin M. Goldenberg, Norwich, N.Y.

[73] Assignee: Morton-Norwich Products, Inc., Norwich, N.Y.

[21] Appl. No.: 704,122

[22] Filed: July 12, 1976

[51] Int. Cl.$^2$ .............................................. A61K 31/34
[52] U.S. Cl. .................................................. 424/285
[58] Field of Search ....................................... 424/285

[56] References Cited

U.S. PATENT DOCUMENTS

| | | | |
|---|---|---|---|
| 3,801,605 | 4/1974 | Carson | 424/285 |
| 3,966,771 | 6/1976 | Pelosi, Jr. | 424/285 |

OTHER PUBLICATIONS

Freund, J. Chem. Soc. 3068–3071, (1952).

*Primary Examiner*—Stanley J. Friedman
*Attorney, Agent, or Firm*—Anthony J. Franze

[57] ABSTRACT

The use of trans-5-(4-chlorophenyl)-2-furanacrylic acid as an anti-inflammatory agent is described.

1 Claim, No Drawings

METHOD FOR TREATING INFLAMMATION

This invention is concerned with the treatment of inflammation and more particularly with the use of trans-5-(4-chlorophenyl)-2-furanacrylic acid for such purpose.

The compound trans-5-(4-chlorophenyl)-2-furanacrylic acid and its preparation have been described in the chemical literature [Freund, J. Chem. Soc. 3068-3071 (1952)]. It has now been discovered that this compound exerts impressive anti-inflammatory activity using the well recognized carrageenin-induced rat paw edema method described by Winter et al. in Proc. Soc. Exp. Biol. Med. 111:544 (1962) which finds wide application and acceptance in detecting substances possessing anti-inflammatory activity. Positive results secured under this method are correlative to successful performance in other species where the need for anti-inflammatory medication is present.

In accordance with the aforementioned method, administration of trans-5-(4-chlorophenyl)-2-furanacrylic acid at a peroral dose of 300 mg/kg to rats caused a 77.5% inhibition of carrageenin-induced edema at four hours post administration and a 74.6% inhibition at 6 hours. At this dose no untoward or unwanted pharmacological effect is observed. Similar administration of aspirin, probably the most popular anti-inflammatory agent, caused a 58.2% and 38.3% inhibition of a carrageenin-induced edema at 4 and 6 hours respectively.

Suitable pharmaceutical forms for peroral administration of trans-5-(4-chlorophenyl)-2-furanacrylic acid comprise tablets and suspensions using excipients and adjuvants common in the pharmaceutical art and capsules, such forms containing from 10 – 500 mg of the acid per unit-dosage form.

What is claimed is:

1. A method of treating inflammation which comprises orally administering to a host in need thereof an anti-inflammatorily amount of trans-5-(4-chlorophenyl)-2-furanacrylic acid in acceptable pharmaceutical dosage form.

* * * * *